US00PP16156P2

(12) United States Plant Patent
Korlipara

(10) Patent No.: US PP16,156 P2
(45) Date of Patent: Dec. 13, 2005

(54) ***VERBASCUM* PLANT NAMED 'PLUM SMOKEY'**

(50) Latin Name: *(Verbascum phoeniceum×V. dumulosum)×V. phoeniceum*
Varietal Denomination: Plum Smokey

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 127 days.

(21) Appl. No.: 10/871,831

(22) Filed: Jun. 18, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP14,167 P2 * 9/2003 Rijnbeek ..... Plt./263
PP14,793 P2 * 5/2004 Oudshoorn ..... Plt./263
2002/0194661 P1 * 12/2002 Heims ..... Plt./263

OTHER PUBLICATIONS http://www.terranovanurseries.com/pages/plantsT3.html.*

* cited by examiner

*Primary Examiner*—Kent Bell
*Assistant Examiner*—W. C. Haas
(74) *Attorney, Agent, or Firm*—Klarquist Sparkman, LLP

(57) ABSTRACT

A new and distinct *Verbascum* plant characterized by numerous red purple colored flowers on numerous short, upright flowering stems, a compact habit, and excellent vigor.

1 Drawing Sheet

Botanical classification: (*Verbascum phoeniceum×V. dumulosum*)×*V. phoeniceum.*

Variety denomination: 'Plum Smokey'.

The present invention relates to a new and distinct cultivar of *Verbascum* hybrid, and given the cultivar name 'Plum Smokey'. *Verbascum* is in the family Scrophulariaceae.

This new cultivar originated from a cross between *Verbascum* 'Jackie' as the seed parent and an unnamed selection of *Verbascum phoeniceum* as the pollen parent. *Verbascum* 'Jackie' is an unpatented plant and a cross between *Verbascum phoeniceum* and *Verbascum dumulosum.*

This new *Verbascum* hybrid is unique in its red purple flower color combined with its *Verbascum* 'Jackie'-like compact habit and short, multiple flowering stems.

This plant is characterized by the following:

1. Large purple red flowers.
2. Numerous upright, branching flowering stems.
3. Compact habit.
4. Short flowering stems.
2. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

BRIEF DESCRIPTION OF THE DRAWING

The photograph shows the whole plant of *Verbascum* 'Plum Smokey' grown in the trial field in bloom in July.

DETAILED PLANT DESCRIPTION

The following is a detailed description of the new *Verbascum* selection based on observations of one-year-old specimens grown in the ground in full sun under typical outdoor conditions in the field in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: (*Verbascum phoeniceum×V. dumulosum*)×*V. phoeniceum.*

Variety denomination: 'Plum Smokey'.

Plant:

*Type.*—Herbaceous perennial.
*Form.*—Clumping basal rosette.
*Hardiness.*—U.S.D.A. Hardiness Zones 5–9.
*Size.*—15 to 20 cm tall and 35 cm wide, not including inflorescence.
*Vigor.*—Excellent.
*Roots.*—With one main tap root, and many fibrous lateral branches, White 155A.
*Stem.*—Much congested, 1 cm deep and wide with no space between nodes.

Leaf:

*Type.*—Simple. Evergreen.
*Arrangement.*—Basal, with 21 to 35 leaves.
*Shape.*—Ovate, sometimes fold or cup up or down from main vein.
*Blade size.*—Grows to 20 cm long and 11.5 cm wide.
*Venation.*—Pinnate.
*Margins.*—Irregularly crenate overall and toothed near base.
*Apex.*—Acute.
*Base.*—Cuneate.

*Surface texture.*—Leathery, rugose, with stellate hairs on both upper and lower surfaces.

*Petiole.*—With 1 to 3 leaf-like appendages, 1 to 1.5 cm long and 0.6 to 0.8 cm wide. Surface texture — Stellate. Color — Yellow Green 145C.

*Leaf color.*—Abaxial — Deep green. Green 137A with lighter main vein, Yellow Green 145D. Adaxial — Between Yellow Green 147B and Green 137C.

Inflorescence:

*Type.*—Panicle.

*Total panicle size.*—39 cm wide and 33 cm high (just the flowers).

*Number of panicles per plant in first flush*—16.

*Cauline leaves.*—5 to 8 in number, 3.5 to 6.5 cm long and 2.5 to 3.2 cm wide, with an acute tip and cuneate base, margins irregularly crenate overall and toothed near base, upper surface is Green 137A with a lighter main vein, Yellow Green 145D and the lower surface is between Yellow Green 147B and Green 137C.

*Flower number.*—Count of 275 flowers on main panicle.

*Peduncle.*—Height — 47 cm. Diameter — 0.8 cm. near base. Surface texture — Stellate. Color — Yellow Green 146C.

*Pedicel.*—Length — 1.5 cm. Surface texture — Glandular hairs. Color — Yellow Green 146A.

*Bloom time.*—July to September in Canby, Oreg.

Flower bud:

*Size.*—1 cm. wide and 0.7 cm. deep.

*Description.*—Pentagonal cushion.

*Surface.*—Sparsely glandular.

*Color.*—Purple 79A.

Flower:

*Type.*—Perfect. Complete. Irregular.

*Shape.*—Rotate, irregular, short tubular.

*Size.*—4.5 cm wide and 1 cm deep including stamens.

*Color.*—Purplish Red, between Purple 77A and Red Purple 70C. Small eye in a ring around stamens and pistil is Yellow Orange 19C to 19D.

*Corolla.*—Petal description — 5 lobes, broadly obovate, margin entire, tip obtuse, base cuneate. Size — 4.5 cm wide and 0.3 cm deep. Surface — Backs sparsely glandular, upper surface glabrous.

*Calyx.*—Sepal description — Stellate, with 5 lobes, each lobe lanceolate with entire margins and an acuminate tip. Size — Grows to 1.2 cm. wide and 0.2 to 0.5 cm. deep. Surface — Glandular hairs on both upper and lower surfaces. Color — Yellow Green 146A on both upper and lower surfaces.

*Stamens.*—Number — 5. Filaments — 0.8 to 0.9 cm. long, Yellow Orange 17A at base and heavily bearded Purple 83B on lower two stamens and Purple 83B topped with White 155A on upper three stamens. Anthers — Kidney shaped. Black 202A before dehiscence, 2 mm long. Pollen — Orange 25A, abundant in quantity.

*Pistil.*—Number — 1. Style — 1.9 cm long, Red Purple 70A. Stigma — Blunt, Yellow Green 146C. Ovary — Yellow Green 146C.

*Fragrance.*—None.

Fertility: Sterile, no fruit or seed produced.

Disease and pests: None observed on plants grown commercially in Canby, Oreg. Powdery mildew and fungal leaf spot are possible. *Verbascum* are susceptible to caterpillars.

COMPARISONS

This new cultivar is very similar in growth habit and flowering habit to *Verbascum* 'Jackie' (unpatented). The greatest difference is the flower color. *V.* 'Jackie' is described as having copper colored buds, which open to pale peach colored flowers and lavender stamens. The new cultivar *Verbascum* 'Plum Smoky' has red purple flowers and the same good qualities of numerous flowering stems, short flowering stems, and compact habit.

I claim:

1. A new and distinct cultivar of *Verbascum* plant as herein illustrated and described.

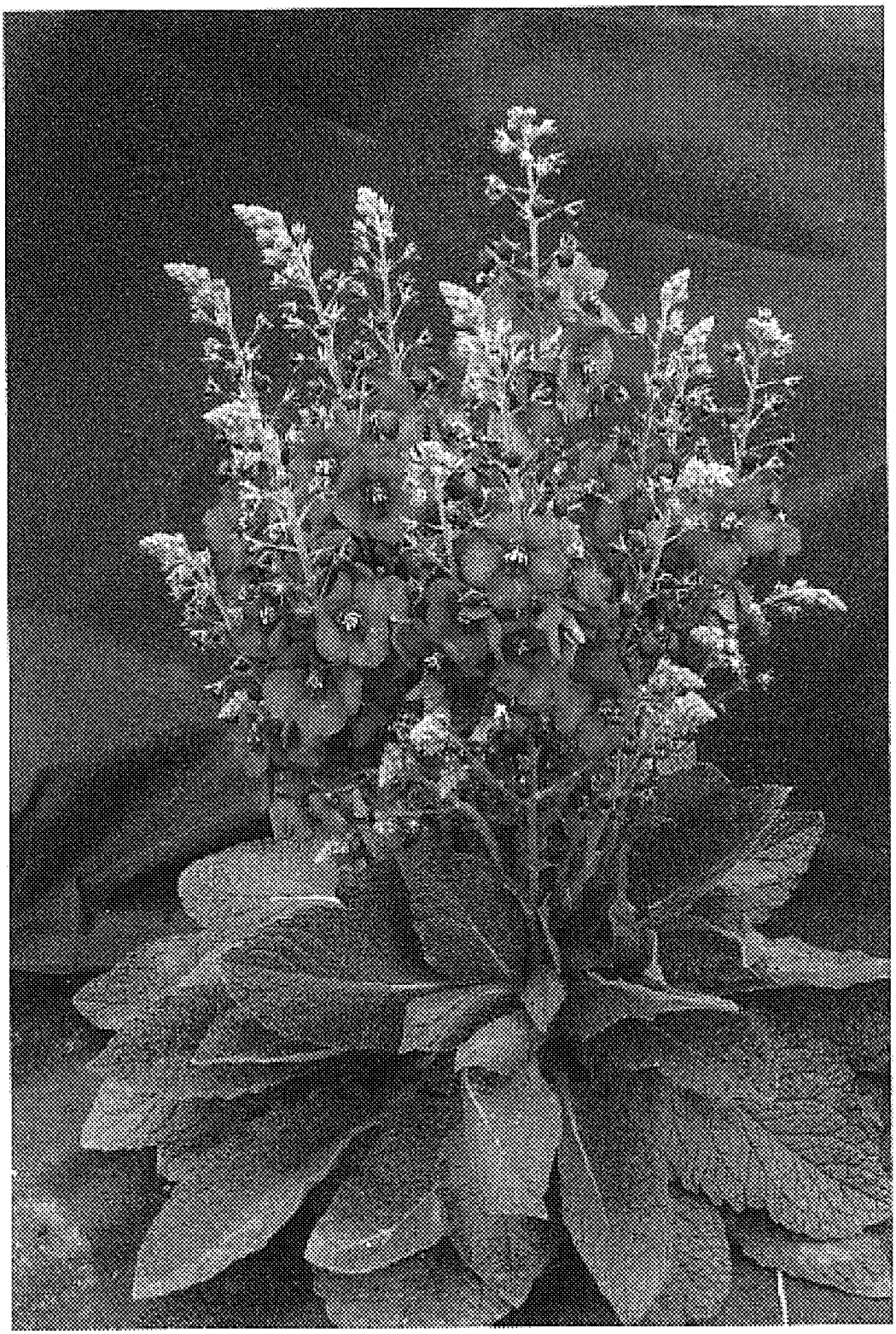

* * * * *